United States Patent
Parroche et al.

(10) Patent No.: US 12,208,087 B2
(45) Date of Patent: Jan. 28, 2025

(54) COMBINATION OF NITAZOXANIDE AND ELAFIBRANOR FOR THE TREATMENT OF IMMUNE DISEASES OR INFLAMMATION

(71) Applicant: GENFIT, Loos (FR)

(72) Inventors: Peggy Parroche, Loos (FR); Robert Walczak, Lille (FR)

(73) Assignee: GENFIT, Loos (FR)

( * ) Notice: Subject to any disclaimer, the term of this patent is extended or adjusted under 35 U.S.C. 154(b) by 689 days.

(21) Appl. No.: 17/599,256

(22) PCT Filed: Apr. 7, 2020

(86) PCT No.: PCT/EP2020/059941
§ 371 (c)(1),
(2) Date: Sep. 28, 2021

(87) PCT Pub. No.: WO2020/208044
PCT Pub. Date: Oct. 15, 2020

(65) Prior Publication Data
US 2022/0175737 A1 Jun. 9, 2022

(30) Foreign Application Priority Data
Apr. 9, 2019 (EP) .................................... 19305463

(51) Int. Cl.
*A61K 31/426* (2006.01)
*A61K 45/06* (2006.01)
(52) U.S. Cl.
CPC ............ *A61K 31/426* (2013.01); *A61K 45/06* (2013.01)

(58) Field of Classification Search
CPC .................................................... A61K 31/426
See application file for complete search history.

(56) References Cited

U.S. PATENT DOCUMENTS 11,033,534 B2 * 6/2021 Foucart ................ A61K 31/426
12,053,456 B2 * 8/2024 Foucart .................... A61P 9/10

FOREIGN PATENT DOCUMENTS

| WO | 2007/081974 A2 | 7/2007 |
| WO | 2018/138352 A1 | 8/2018 |
| WO | 2018/167103 A1 | 9/2018 |
| WO | 2018/193006 A1 | 10/2018 |

OTHER PUBLICATIONS

Walczak et al, "Elafibranor and nitazoxanide synergize to reduce fibrosis in a NASH model", Journal of Hepatology, vol. 68, 2018, pp. S352-S353.
Man et al: "Tumor-Infiltrating Immune Cells Promoting Tumor Invasion and Metastasis: Existing Theories", Journal of Cancer, vol. 4, No. 1, 2013, pp. 84-95.
International Search Report and Written Opinion of PCT/EP2020/059941, mailed on Jun. 17, 2020.

* cited by examiner

*Primary Examiner* — Golam M Shameem
(74) *Attorney, Agent, or Firm* — Leason Ellis LLP

(57) ABSTRACT

The present invention relates to a combination product comprising (i) nitazoxanide (NTZ) or an analogue thereof, and (ii) a PPAR agonist, for use in the treatment of an immune diseases or inflammation.

10 Claims, 1 Drawing Sheet

COMBINATION OF NITAZOXANIDE AND ELAFIBRANOR FOR THE TREATMENT OF IMMUNE DISEASES OR INFLAMMATION

The present invention relates to a combination product comprising (i) nitazoxanide (NTZ) or an analogue thereof, and (ii) a PPAR agonist, for use in the treatment of an immune disease or inflammation.

The activation of immune response can be a triggering event for a number of diseases. For example, infiltration of lymphocytes in organs can result in the activation of pathophysiological events. In the liver, the infiltration and activation of an immune response can be the triggering event for the induction of fibrosis, a phenomenon observed in a number of liver diseases such as non-alcoholic steatohepatitis (NASH), non-alcoholic fatty liver disease (NAFLD), alcoholic steatohepatitis (ASH), primary biliary cholangitis (PBC) and primary sclerosing cholangitis (PSC).

There is thus a need to provide new treatment strategies for stopping or decreasing lymphocyte infiltration, or for stopping or decreasing lymphocyte activation in a cell, tissue or organ of interest.

The present invention stems from the surprising observation that a combination of (i) NTZ or an analogue thereof with (ii) a PPAR agonist, prevents T cell infiltration into the liver.

Accordingly, the invention relates to a combination product comprising:
(i) a compound of formula (I) as defined below, or a pharmaceutically acceptable salt thereof; and
(ii) a compound of formula (II) as defined below, or a pharmaceutically acceptable salt thereof;
for use in a method for the treatment of an immune disease or inflammation.

The invention further relates to a combination product comprising:
(i) a compound of formula (I) as defined below, or a pharmaceutically acceptable salt thereof; and
(ii) a compound of formula (II) as defined below, or a pharmaceutically acceptable salt thereof;
for use in a method for reducing or stopping immune cell infiltration into a tissue or organ of interest.

Compounds of formula (I), which include NTZ and analogues thereof, are defined as follows:

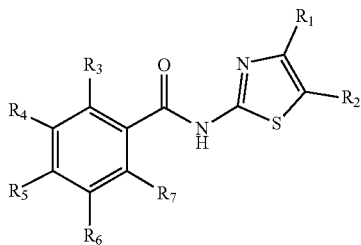

(I)

in which:
R1 represents a hydrogen atom, a deuterium atom, a halogen atom, a (C6-C14)aryl group, a heterocyclic group, a (C3-C14)cycloalkyl group, a (C1-C6)alkyl group, a sulfonyl group, a sulfoxyde group, a (C1-C6)alkylcarbonyl group, a (C1-C6)alkyloxy, a carboxylic group, a carboxylate group, a nitro group (NO2), an amino group (NH2), a (C1-C6)alkylamino group, an amido group, a (C1-C6)alkylamido group or a (C1-C6)dialkylamido group;

R2 represents a hydrogen atom, a deuterium atom, a NO2 group, a (C6-C14)aryl group, a heterocyclic group, a halogen atom, a (C1-C6)alkyl group, a (C3-C14)cycloalkyl group, a (C2-C6)alkynyl group, a (C1-C6)alkyloxy group, a (C1-C6)alkylthio group, a (C1-C6)alkylcarbonyl group, a (C1-C6)alkylcarbonylamino group, a (C6-C14)arylcarbonylamino group, a carboxylic or carboxylate group, an amido group, a (C1-C6)alkylamido group, a (C1-C6)dialkylamido group, a NH2 group or a (C1-C6)alkylamino group;

or R1 and R2, together with the carbon atoms to which they are attached, form a substituted or unsubstituted 5- to 8-membered cycloalkyl, heterocyclic or aryl group;

R3, R4, R5, R6, and R7, identical or different, represent a hydrogen atom, a deuterium atom, a halogen atom, a hydroxyl group, a (C1-C6)alkylcarbonyl group, an (C1-C6)alkyl group, an (C1-C6)alkyloxy group, an (C1-C6)alkylthio group, an (C1-C6)alkylcarbonyloxy group, an (C6-C14)aryloxy group, a (C6-C14)aryl group, a heterocyclic group, a (C3-C14)cycloalkyl group, a NO2 group, a sulfonylaminoalkyle group, an NH2 group, an amino(C1-C6)alkyl group, an (C1-C6)alkylcarbonylamino group, a carboxylic group, a carboxylate group or a R9 group;

R9 represents a O—R8 group or an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or a moiety of formula (A):

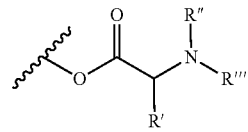

(A)

wherein R' represents an (C1-C6)alkyl group, an (C2-C6)alkenyl group, an (C2-C6)alkynyl group, a (C3-C14)cycloalkyl group, (C3-C14)cycloalkylalkyl group, a (C3-C14)cycloalkyl(C2-C6)alkenyl group, a (C3-C14)cycloalkenyl group, a (C3-C14)cycloalkenyl(C1-C6)alkyl group, a (C3-C14)cycloalkenyl(C2-C6)alkenyl group or a (C3-C14)cycloalkenyl(C2-C6)alkynyl group; wherein R" and R''', independently, represent a hydrogen atom, an (C1-C6)alkyl group, or a nitrogen protecting group; and R8 represents a hydrogen atom, a deuterium atom, a glucuronidyl group, or a group wherein, R8a, R8b and R8c, identical or different, represent a hydrogen atom or a deuterium atom.

In a particular embodiment, the compound of formula (I) is as follows:
R1 represents a hydrogen atom, a deuterium atom, a halogen atom, a (C6-C14)aryl group, a heterocyclic group, a (C3-C14)cycloalkyl group, a (C1-C6)alkyl group, a sulfonyl group, a sulfoxyde group, a (C1-C6) alkylcarbonyl group, a (C1-C6)alkyloxy, a carboxylic group, a carboxylate group, a NO₂ group, a NH2 group, a (C1-C6)alkylamino group, an amido group, a (C1-C6)alkylamido group or a (C1-C6)dialkylamido group;

R2 represents a hydrogen atom, a deuterium atom, a NO2 group, a (C6-C14)aryl group, a heterocyclic group, a halogen atom, a (C1-C6)alkyl group, a (C3-C14)cycloalkyl group, a (C2-C6)alkynyl group, a (C1-C6)alkyloxy group, a (C1-C6)alkylthio group, a (C1-C6)alkylcarbonyl group, a (C1-C6)alkylcarbonylamino group, a (C6-C14)arylcarbonylamino group, a carboxylic or carboxylate group, an amido group, a (C1-C6)alkylamido group, a (C1-C6)dialkylamido group, a NH₂ group, a (C1-C6)alkylamino group;

or R1 and R2, together with the carbon atoms to which they are attached, form a substituted or unsubstituted 5- to 8-membered cycloalkyl, heterocyclic or aryl group;

R3 represents a hydrogen atom, a deuterium atom, a halogen atom, a O—R8 group, a (C1-C6)alkylcarbonyl group, an (C1-C6)alkyl group, an (C1-C6)alkyloxy group, an (C1-C6)alkylthio group, an (C1-C6)alkylcarbonyloxy group, an (C6-C14)aryloxy group, a (C6-C14)aryl group, a heterocyclic group, a (C3-C14)cycloalkyl group a NO2, a sulfonylaminoalkyle group, an NH2 group, an amino(C1-C6)alkyl group, an (C1-C6)alkylcarbonylamino group, a carboxylic group, a carboxylate group, an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or a moiety of formula (A):

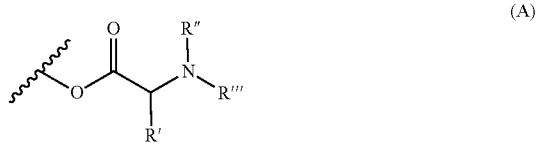

(A)

wherein R' represents an (C1-C6)alkyl group, an (C2-C6) alkenyl group, an (C2-C6)alkynyl group, a (C3-C14) cycloalkyl group, (C3-C14)cycloalkylalkyl group, a (C3-C14)cycloalkyl(C2-C6)alkenyl group, a (C3-C14) cycloalkenyl group, a (C3-C14)cycloalkenyl(C1-C6) alkyl group, a (C3-C14)cycloalkenyl(C2-C6)alkenyl group or a (C3-C14)cycloalkenyl(C2-C6)alkynyl group; wherein R" and R''', independently, represent a hydrogen atom, an (C1-C6)alkyl group, or a nitrogen protecting group;

R8 represents a hydrogen atom, a deuterium atom, or a

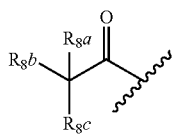

group wherein, R8a, R8b and R8c, identical or different, represent a hydrogen atom or a deuterium atom; and R4, R5, R6, and R7, identical or different, represent a hydrogen atom, a deuterium atom, a halogen atom, a hydroxyl group, an (C1-C6)alkylcarbonyl group, an (C1-C6)alkyl group, an (C1-C6)alkyloxy group, an (C1-C6)alkylthio group, an (C1-C6)alkylcarbonyloxy group, an (C6-C14)aryloxy group, an (C6-C14)aryl group, a heterocyclic group, a (C3-C14)cycloalkyl group, a NO2, a sulfonylamino(C1-C6)alkyl group, an NH2 group, an amino(C1-C6)alkyl group, an (C1-C6) alkylcarbonylamino group, a carboxylic group, a carboxylate group, an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or a moiety of formula (A):

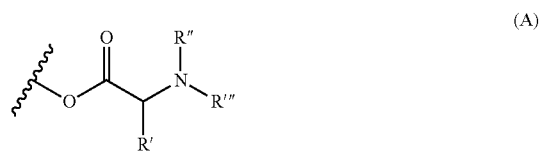

(A)

wherein R' represents an (C1-C6)alkyl group, an (C2-C6) alkenyl group, an (C2-C6)alkynyl group, a (C3-C14) cycloalkyl group, (C3-C14)cycloalkyl(C1-C6)alkyl group, a (C3-C14)cycloalkyl(C1-C6)alkenyl group, a (C3-C14)cycloalkenyl group, a (C3-C14)cycloakenyl (C1-C6)alkyl group, a (C3-C14)cycloalkenyl(C2-C6) alkenyl group, a (C3-C14)cycloalkenyl(C2-C6)alkynyl group; R" and independently, represent a hydrogen atom, an (C1-C6)alkyl group, or a nitrogen protecting group.

In a particular embodiment, in the compound of formula (I) of the present invention:

an alkyl group may be a substituted or unsubstituted (C1-C6)alkyl group, in particular a substituted or unsubstituted (C1-C4)alkyl group;

an alkynyl group may be a substituted or unsubstituted (C2-C6)alkynyl group;

a cycloalkyl group may be a substituted or unsubstituted (C3-C14)cycloalkyl group an alkyloxy group may be a substituted or unsubstituted (C1-C6)alkyloxy group, such as a substituted or unsubstituted (C1-C4)alkyloxy group;

an alkylthio group may be a substituted or unsubstituted (C1-C6)alkylthio group, such as a substituted or unsubstituted (C1-C4)alkylthio group;

an alkylamino group may be a (C1-C6)alkylamino group, such as a (C1-C4)alkylamino group;

a dialkylamino group may be a (C1-C6)dialkylamino group, such as a (C1-C4)dialkylamino group;

an aryl group may be a substituted or unsubstituted (C6-C14)aryl group, such as a substituted or unsubstituted (C6-C14)aryl group;

a heterocyclic group may be a substituted or unsubstituted heterocycloalkyl or heteroaryl group.

Nitrogen protecting groups are well known to those skilled in the art, such as those described in the literature, as, for example, in the book "Greene's Protective Groups in Organic Synthesis" (Wut and Greene (2007), Greene's Protective Groups in Organic Synthesis, Fourth Edition, John Wiley & Sons).

In a specific embodiment, the compound of formula (I) is a compound of formula (I'):

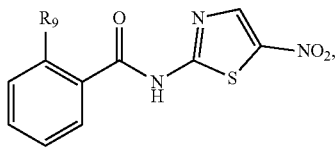
(I')

in which R9 represents a hydrogen atom, a deuterium atom, a O—R8 group (R8 being as defined above), or an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or a moiety of formula (A):

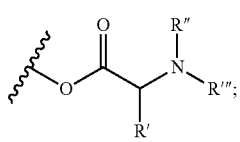
(A)

wherein R' represents an (C1-C6)alkyl group, an (C2-C6) alkenyl group, an (C2-C6)alkynyl group, a (C3-C14) cycloalkyl group, (C3-C14)cycloalkyl(C1-C6)alkyl group, a (C3-C14)cycloalkyl(C1-C6)alkenyl group, a (C3-C14)cycloalkenyl group, a (C3-C14)cycloakenyl (C1-C6)alkyl group, a (C3-C14)cycloalkenyl(C2-C6) alkenyl group, a (C3-C14)cycloalkenyl(C2-C6)alkynyl group; R" and R''', independently, represent a hydrogen atom, an (C1-C6)alkyl group, or a nitrogen protecting group or a pharmaceutically acceptable salt thereof.

In a particular embodiment, the compound of formula (I) is selected from:

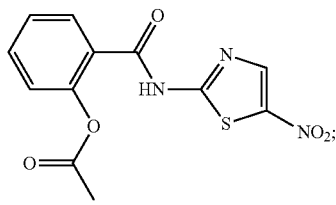

NTZ

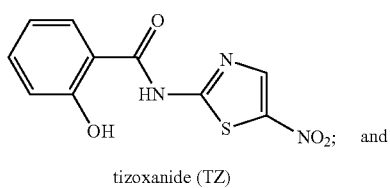

tizoxanide (TZ)

and

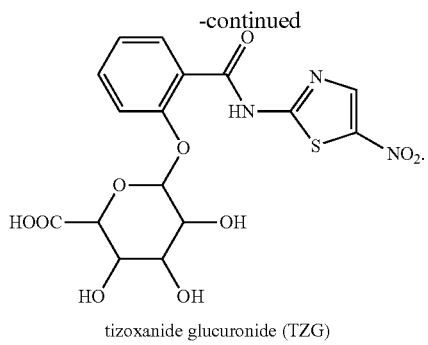

tizoxanide glucuronide (TZG)

In another embodiment, the compound of formula (I') is such that
R8a, R8b and R8c, identical or different, represent a hydrogen atom or a deuterium
atom; and/or
R1, R3, R4, R5, and R6, identical or different, represent a hydrogen atom or a deuterium atom with the proviso that R1, R2, R8a, R8b, R8c, R3, R4, R5, and R6 are not simultaneously a hydrogen atom.

In a particular embodiment, the compound of formula (I) is [(5-nitro-1,3-thiazol-2-yl)carbamoyl]phenyl(d3)ethanoate, 2-[(5-nitro-1,3-thiazol-2-yl)carbamoyl]phenyl (d2) ethanoate; or 2-[(5-nitro-1,3-thiazol-2-yl)carbamoyl]phenyl (d1) ethanoate.

In another particular embodiment, the compound of formula (I) is 2-(5-nitrothiazol-2-ylcarbamoyl)phenyl 2-amino-3,3-dimethylbutanoate, in particular (S)-2-(5-nitrothiazol-2-ylcarbamoyl)phenyl 2-amino-3,3-dimethylbutanoate, or a pharmaceutically acceptable salt thereof such as its hydrochloride salt (RM5061) of formula:

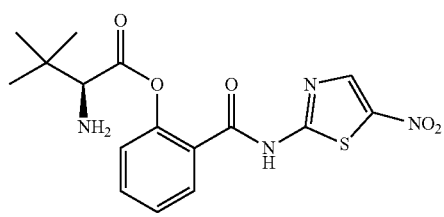

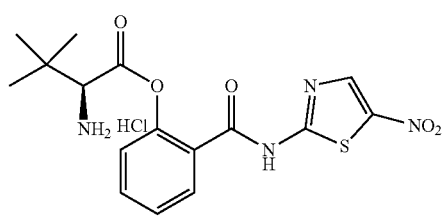

In another particular embodiment, the compound of formula (I) is 2-(5-nitrothiazol-2-ylcarbamoyl)phenyl 2-amino-3-methylpentanoate, in particular (2S,3S)-2-(5-nitrothiazol-2-ylcarbamoyl)phenyl 2-amino-3-methylpentanoate, or a pharmaceutically acceptable salt thereof such as its hydrochloride salt (RM5066) of formula:

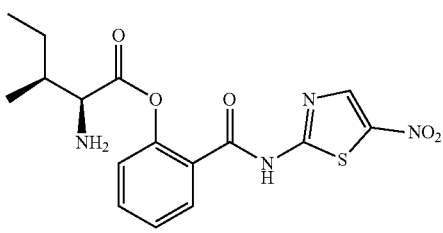 [SMILES: CC[C@H](C)[C@H](N)C(=O)Oc1ccccc1C(=O)Nc1ncc([N+](=O)[O-])s1]

In another particular embodiment, the compound of formula (I) is 2-(5-chlorothiazol-2-ylcarbamoyl)phenyl 2-amino-3,3-dimethylbutanoate, in particular (S)-2-(5-chlorothiazol-2-ylcarbamoyl)phenyl 2-amino-3,3-dimethylbutanoate, or a pharmaceutically acceptable salt thereof such as its hydrochloride salt (RM5064) of formula:

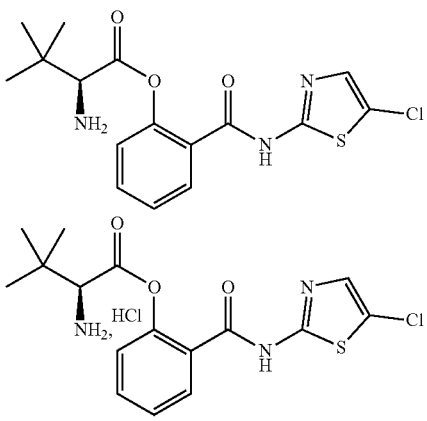

In another particular embodiment, the compound of formula (I) is -2-(5-chlorothiazol-2-ylcarbamoyl)phenyl 2-amino-3-methylpentanoate, in particular (2S,3S)-2-(5-chlorothiazol-2-ylcarbamoyl)phenyl 2-amino-3-methylpentanoate, or a pharmaceutically acceptable salt thereof such as its hydrochloride salt (RM5065) of formula:

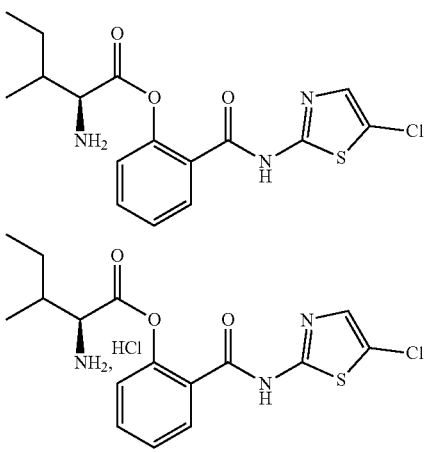

In a particular embodiment, component (i) is NTZ, TZ, TZG or a pharmaceutically acceptable salt thereof. In another particular embodiment, component (i) is NTZ, TZ or a pharmaceutically acceptable salt thereof. In yet another embodiment, component (i) is NTZ or a pharmaceutically acceptable salt thereof Synthesis of NTZ or analogues can be for example carried out as described in (Rossignol et al. (1975). 2-Benzamido-5-nitrothiazoles, S. P. R. L. Phavic, Belg. 11 pp.), or by any other way of synthesis known by a person skilled in the art.

Compounds of formula (II) are PPAR agonists, and are defined as follows:

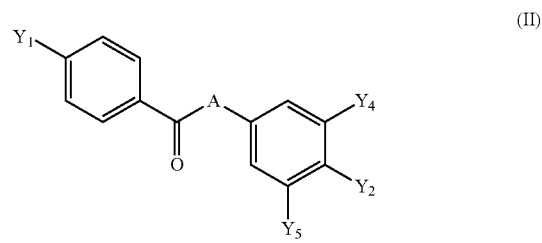

(II)

in which:
Y1 represents a halogen, a Ra, or Ga-Ra group;
A represents a CH=CH or a CH2-CH2 group;
Y2 represents a Gb-Rb group;
Ga and Gb, identical or different, represent an atom of oxygen or sulfur;
Ra represents a hydrogen atom, an unsubstituted (C1-C6) alkyl group, a (C6-C14)aryl group or a (C1-C6)alkyl group that is substituted by one or more halogen atoms, a (C1-C6)alkoxy or a (C1-C6)alkylthio group, (C3-C14)cycloalkyl groups, (C3-C14)cycloalkylthio groups or heterocyclic groups;
Rb represents a (C1-C6)alkyl group substituted by at least a —COORc group, wherein Rc represents a hydrogen atom, or a (C1-C6)alkyl group that is substituted or not by one or more halogen atoms, (C3-C14)cycloalkyl groups, or heterocyclic groups; and
Y4 and Y5, identical or different, representing a (C1-C6) alkyl group that is substituted or not by one or more halogen atoms, (C3-C14)cycloalkyl groups or heterocyclic groups.

In a particular embodiment of the compound of formula (II):
Y1 represents a halogen, a Ra, or a Ga-Ra group;
A represents a CH=CH group;
Y2 represents a Gb-Rb group;
Ga and Gb, identical or different, represent an atom of oxygen or sulfur;
Ra represents a (C1-C6)alkyl or (C3-C14)cycloalkyl group, in particular a (C1-C6)alkyl or (C3-C14)cycloalkyl group substituted or not by one or more halogen atoms;
Rb represents a (C1-C6)alkyl group substituted by a —COOR3 group, wherein Rc represents a hydrogen atom or an alkyl group having from one to four carbon atoms; and
Y4 and Y5 independently represent a (C1-C4)alkyl group.

In a particular embodiment of the compound of formula (II):
Y1 represents a Ra or Ga-Ra group;
A represents a CH2-CH2 group;
Y2 represents a Gb-Rb group;
Ga represents an atom of oxygen or sulfur and Gb represents an atom of oxygen;
Ra represents a (C1-C6)alkyl or (C3-C14)cycloalkyl group;
Rb represents a (C1-C6)alkyl group substituted by at least a —COORc group, wherein Rc represents a hydrogen atom or (C1-C4)alkyl group; and Y4 and Y5 independently represent a (C1-C4)alkyl group.

In a particular embodiment of the compound of formula (II):
Y1 represents a halogen atom or a Ra or Ga-Ra group;
A represents a CH2-CH2 group;
Y2 represents a Gb-Rb group;
Ga represents an atom of oxygen or sulfur and Gb represents an atom of oxygen;
Ra represents a (C1-C6)alkyl or (C3-C14)cycloalkyl group that is substituted by one or more halogen atoms;
Rb represents a (C1-C6)alkyl group substituted or not by one or more halogen atoms and substituted by at least a —COORc group, wherein Rc represents a hydrogen atom or a (C1-C4)alkyl group; and
Y4 and Y5 represent a (C1-C4)alkyl group.

In a particular embodiment of the compound of formula (II), Gb is an oxygen atom and Rb is (C1-C6)alkyl group substituted by a —COORc group, wherein Rc represents a hydrogen atom or an unsubstituted linear or branched (C1-C4)alkyl group.

In a particular embodiment of the compound of formula (II), Y1 is a (C1-C6)alkylthio group that comprises a (C1-C6)alkyl group that is linear or branched that is substituted or not by one or more halogen atoms.

In a particular embodiment, the compound of formula (II) is selected in the group consisting of 1-[4-methylthiophenyl]-3-[3,5-dimethyl-4-carboxydimethylmethyloxy phenyl] prop-2-en-1-one (Elafibranor, ELA or GFT505), 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl]prop-2-en-1-one, 1-[4-trifluoromethylphenyl]-3-[3,5-dimethyl-4-tertbutyloxycarbonyl dimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl]prop-2-en-1-one, 1-[4-trifluoromethyloxyphenyl]-3-[3,5-dimethyl-4-carboxydimethylmethyl oxyphenyl]prop-2-en-1-one, 2-[2,6-dimethyl-4-[3-[4-(methylthio)phenyl]-3-oxo-propyl]phenoxy]-2-methylpropanoic acid, 2-[2,6-dimethyl-4-[3-[4-(methylthio)phenyl]-3-oxo-propyl]phenoxy]-2-methyl-propanoic acid isopropyl ester, and pharmaceutically acceptable salts thereof.

In a preferred embodiment of the invention, the compound of formula (II) is ELA or a pharmaceutically acceptable salt thereof.

According to the invention the compound of formula (I) and the compound of formula (II) can be selected so that the combination of said compounds provides a synergistic action against immune cell infiltration. Such synergy may be determined according to methods well-known in the art, such as by using the Excess Over Bliss (EOB, or Excess over Highest Single Agent) method. This method, employed by the FDA for approval of combination drug products, assumes that the expected combination effect is superior to the effect obtained with the best component of the combination when taken individually. As demonstrated in the examples, the combination of NTZ and ELA produces a synergistic action against immune infiltration.

Accordingly, in a particular embodiment, the compound of formula (I) is NTZ, TZ or a pharmaceutically acceptable salt thereof, and the compound of formula (II) is ELA or a pharmaceutically acceptable salt thereof.

In a more preferred embodiment, the compound of formula (I) is NTZ or a pharmaceutically acceptable salt thereof, and the compound of formula (II) is ELA or a pharmaceutically acceptable salt thereof.

In another embodiment, the compound of formula (I) is NTZ and the compound of formula (II) is ELA.

In a particular embodiment, the combination product of the invention is a pharmaceutical composition comprising both the compound of formula (I) and the compound of formula (II), in a pharmaceutically acceptable carrier.

In another embodiment, the combination product of the invention is a kit of parts comprising the compound of formula (I) and the compound of formula (II), for sequential, separate or simultaneous use. In this embodiment, each of the compounds can be formulated in different pharmaceutical compositions.

The pharmaceutical compositions used in the invention can comprise one or several excipients or vehicles, acceptable within a pharmaceutical context (e.g. saline solutions, physiological solutions, isotonic solutions, etc., compatible with pharmaceutical usage and well-known by one of ordinary skill in the art). These compositions can also comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc. The compounds of formula (I) and (II) can be formulated for enteral or parenteral administration. For example, the compounds can be formulated for oral, intravascular (e.g. intravenous or intra-arterial), intramuscular, intraperitoneal, subcutaneous, transdermal or nasal administration. The formulation can be a solid or liquid dosage form. Illustrative formulations include, without limitation, an injectable suspension, or suspension for oral ingestion, a gel, an oil, a pill, a tablet, a suppository, a powder, a capsule, an aerosol, an ointment, a cream, a patch, or means of galenic forms for a prolonged and/or slow release. For this kind of formulation, agents such as cellulose, carbonates or starches can be advantageously used.

The compounds of formula (I) and (II) can be formulated as pharmaceutically acceptable salts, particularly acid or base salts compatible with pharmaceutical use. Salts of compounds of formula (I) and (II) include pharmaceutically acceptable acid addition salts, pharmaceutically acceptable base addition salts, pharmaceutically acceptable metal salts, ammonium and alkylated ammonium salts. These salts can be obtained during the final purification step of the compound or by incorporating the salt into the previously purified compound.

The combination product of the invention is for use in a method for the treatment of a disease that involves or is characterized by the infiltration of a tissue or organ with immune cells. Such diseases include, for example, immune diseases and inflammation.

The term "treatment" or "treating" refers to the curative or preventive treatment of a disease in a subject in need thereof. The treatment involves the administration of the combination of the invention to a subject having a declared disease, to prevent, cure, delay, reverse, or slow down the progression of the disease, improving thereby the condition of the subject. The combination product can also be administered to a subject that is healthy or at risk of developing a disease. The subject to be treated is a mammal, preferably a human. The subject to be treated according to the invention can be selected on the basis of several criteria associated to the specific disease the treatment of which is sought such as previous drug treatments, associated pathologies, genotype, exposure to risk factors, viral infection, as well as on the basis of the detection of any biomarker relevant to the disease.

Illustrative tissue or organ of interest include, without limitation, liver, kidney, skin, epidermis, endodermis, muscle, tendon, cartilage, heart, pancreas, lung, uterus, nervous system, testis, penis, ovary, adrenal gland, artery, vein, colon, intestine (e.g. small intestine), biliary tract, soft tissue (e.g. mediastinum or retroperitoneum), bone marrow, joint (e.g. knee, shoulder or other joints) and stomach. In a preferred embodiment, the tissue or organ of interest is the liver.

The invention thus relates, without limitation, to the combination product of the invention for use in a method for the treatment of an immune disease or inflammation of the liver, kidney, skin, epidermis, endodermis, muscle, tendon, cartilage, heart, pancreas, lung, uterus, nervous system, testis, penis, ovary, adrenal gland, artery, vein, colon, intestine (e.g. small intestine), biliary tract, a soft tissue (e.g. mediastinum or retroperitoneum), bone marrow, joint (e.g. knee, shoulder or other joints) or stomach. In a preferred embodiment, the combination product of the invention is for use in a method for the treatment of an immune disease or inflammation of the liver, in particular of an inflammation of the liver. In a further particular embodiment, the combination product of the invention is for use in a method for the treatment of an inflammation of the liver associated to NASH, NAFLD, ASH, PBC or PSC. In yet another embodiment, the combination product is for use in a method for the treatment of NASH-associated inflammation.

Illustrative immune cells whose infiltration can be reduced or stopped include granulocytes or agranulocytes. The immune cells also include myeloid cells or lymphoid cells. Further illustrative immune cell types include, without limitation, neutrophils, eosinophils, basophils, lymphocytes and monocytes. Among the lymphocytes, T cell, B cell and NK cell infiltration can be reduced or stopped, in particular T cell infiltration.

In a particular embodiment, the combination product of the invention is for use in a method for treating a disease involving or characterized by T cell infiltration into a tissue or organ of interest. More specifically, the combination product is for use in a method for treating a disease involving or characterized by T cell infiltration into the liver.

In another aspect, the combination product is for use in a method for reducing or stopping immune cell infiltration associated to a disease. In a particular embodiment, the combination product is for use in a method for reducing or stopping immune cell infiltration occurring in the liver. Illustrative uses include, without limitation, the reduction or stopping of immune cell infiltration into the liver associated to NASH, ASH, NAFLD, PBC or PSC. In a specific embodiment, the immune cells are T cells. In a further specific embodiment, the combination product is for use in a method for reducing or stopping NASH-associated T cell infiltration into the liver.

The frequency and/or dose relative to the administration can be adapted by one of ordinary skill in the art, in function of the subject to be treated, the disease to be treated, the stage of the disease, the form of administration, etc. Typically, the compound of formula (I), in particular NTZ or a pharmaceutically acceptable salt thereof, can be administered at a dose comprised between 0.01 mg/day to 4000 mg/day, such as from 50 mg/day to 2000 mg/day, and particularly from 100 mg/day to 1000 mg/day, more particularly from 500 mg/day to 1000 mg/day. The compound of formula (II), in particular ELA or a pharmaceutically acceptable salt thereof, can be administered at a dose comprised between 0.01 mg/day to 4000 mg/day, such as from 1 mg/day to 2000 mg/day, in particular from 25 to 1000 mg/day, particularly from 50 to 200 mg/day, and even more particularly from 80 mg/day to 120 mg/day. In a particular embodiment, the compound of formula (I) and the compound of formula (II) are orally administered at these doses, e.g. in the form of a pill or tablet. In a further particular embodiment, the compound of formula (I) and the compound of formula (II) are in the same composition, such as oral compositions (e.g. pills or tablets) and are administered at these doses. In another embodiment, the compound of formula (I) and the compound of formula (II) are in different compositions, such as oral compositions (e.g. pills or tablets) and are administered at these doses. In another embodiment, the compounds of formula (I) and (II) are in different compositions and the compound of formula (I) is in the form of a liquid suspension for oral ingestion and the compound of formula (II) is in the form of a tablet.

Administration can be performed daily or even several times per day, if necessary. The duration of the treatment will depend on the specific disease to be treatment. For example, ghe administration can be performed during one or several days, such as during at least one day, at least two days, at least three days, at least four days, at least five days, at six two days or at least seven days. Alternatively, the administration can be performed for at least one week, at least two weeks, at least four weeks. For chronic diseases, administration can be considered for more than four weeks, such as for at least one month, two months, three months, four months, five months, six months or more than six months, such as for at least one year or several years. In some cases, the combination product of the invention can be administered during the lifetime of the subject.

The invention is further described with reference to the following, non-limiting, examples.

6 week-old C57BL/6 mice were fed a control (CSAA) diet, CDAA+1% CHOL (CDAA/c) diet, or CDAA/c diet supplemented with NTZ 100 mg/kg/day alone, ELA 1 mg/kg/day alone or combined NTZ 100 mg/kg/day /ELA 1 mg/kg/day for 12 weeks. After the sacrifice, RNAseq analyses were performed on liver samples.

Figure 1:
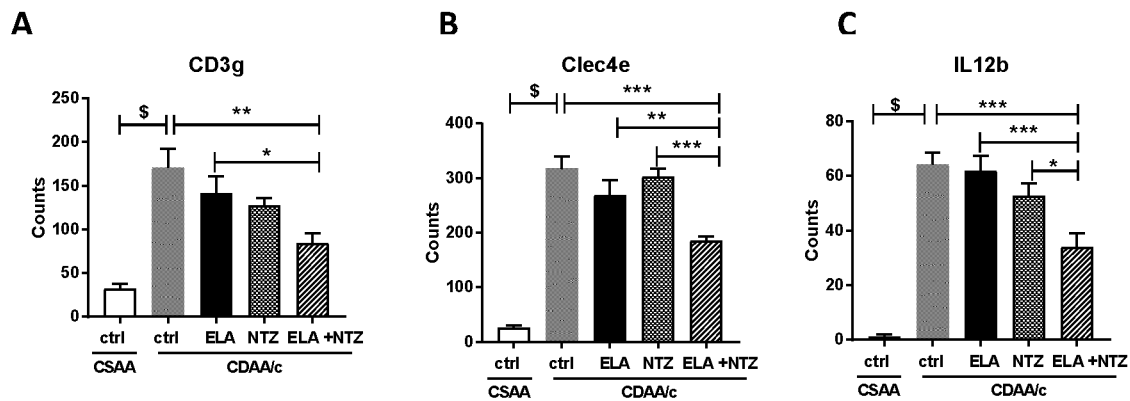
FIG. 1: The chronic oral administration of ELA combined with NTZ significantly reduces the hepatic expression at mRNA levels of several markers associated with T cell infiltration and activation (A: CD3g; B: Clec4e, C:IL12b).
Figure 2:
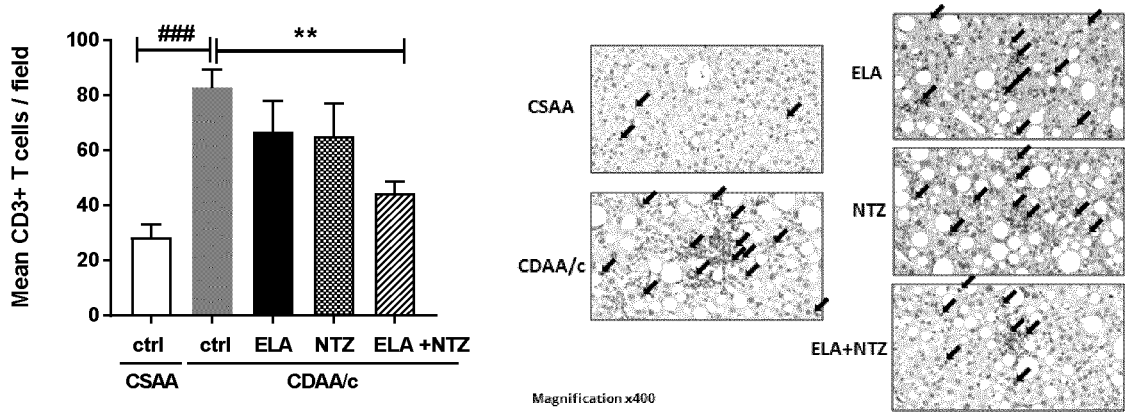

FIG. 2: The chronic oral administration of ELA combined with NTZ significantly reduces T-cell infiltration into the Liver.

6 week-old C57BL/6 mice were fed a control (CSAA) diet, CDAA+1% CHOL (CDAA/c) diet, or CDAA/c diet supplemented with NTZ 100 mg/kg/day alone, ELA 1 mg/kg/day alone or combined NTZ 100 mg/kg/day /ELA 1 mg/kg/day for 12 weeks. The number of CD3+ cells were determined by immunohistochemistry and quantified (FIG. A). Representative images of CD3+ staining for each group are shown on FIG. B (Magnification ×400).

MATERIAL & METHODS

Statistical Analysis

Experimental results were expressed as mean±SEM and plotted as bar graphs. Statistical analyses were performed using Prism Version 7, as follows:

CSAA vs CDAA+1% chol groups were compared by a Mann-Whitney test ($: p<0.05; $$: p<0.01; $$$: p<0.001).

Treatment groups were compared to CDAA+1% chol diet or to other treatment groups by one-way ANOVA and uncorrected Fisher's LSD post-hoc (*: p<0.05; : p<0.01; *: p<0.001).

Evaluation of Elafibranor, Nitazoxanide and the combination of Elafibranor+Nitazoxanide in a chronic CDAA+1% cholesterol model of fibrosing NASH (12 weeks)

Experimental Design

The choline-deficient and L-amino acid-defined (CDAA) diet lacks choline, which is essential for hepatic β-oxidation and very low density lipoprotein production, and is believed to induce hepatocellular steatosis. Subsequently, lipid peroxidation and oxidative stress lead to lobular inflammation, comprehensively resulting in fibrosis.

In the current study, the preventive effects of NTZ 100 mg/kg/day, ELA 1 mg/kg/day and the combination of both were assessed in a murine model. 6 week-old male C57Bl/6J mice were fed a control (CSAA) diet (n=8), CDAA+1% cholesterol diet (n=12), or CDAA+1% cholesterol diet supplemented with NTZ 100 mg/kg/day (n=8), ELA 1 mg/kg/day (n=8) or combined drugs (NTZ 100 mg/kg/day coadministered with ELA 1 mg/kg/day (n=8)) for 12 weeks. The food was purchased from Ssniff® company (Soest, Germany). Nitazoxanide (Interchim, Ref #RQ550), Elafibranor (Genfit) or both compounds were incorporated by Ssniff® into CDAA+1% chol diet in powder form to the required dose.

The body weight and the food intake were monitored twice per week. On the last day of treatment, mice were sacrificed after a 6 h fasting period. The liver was rapidly excised for transcriptomic and histological studies.

All animal procedures were performed according to standard protocols and in accordance with the standard recommendations for the proper care and use of laboratory animals.

Transcriptomic Studies

RNA Extraction

Hepatic Total RNA was isolated using Nucleospin® 96 Kit (Macherey Nagel) following manufacturer's instructions. 150 ng of total RNA were reverse transcribed in cDNA using M-MLV-RT (Moloney Murine Leukemia Virus Reverse Transcriptase) (Invitrogen cat #28025) in presence of RT buffer 1× (Invitrogen cat #P/NY02321), 1 mM DTT (Invitrogen cat #P/NY00147), 0.5 mM dNTPs (Promega), 200 ng pdN6 (Roche cat #11034731001) and 40 U of Ribonuclease inhibitor (Promega cat #N2515).

RNA-Sequencing:

Upon measurement of RNA samples concentration by nanodrop, the quality was assessed using bioanalyser. Libraries were prepared using the Illumina TruSeq stranded mRNA LT kit and mRNA were sequenced using a NextSeq 500 device (paired-end sequence, 2×75 bp), with a High Output flow cell.

RNA-Seq Data Analysis:

Reads were cleaned using Trimmomatic v.0.36 with the following parameters: SLIDINGWINDOW:5:20 LEADING:30 TRAILING:30 MINLEN:60. Then reads were aligned on the genome reference (*Mus musculus* GRCm38.90) with rnacocktail using hisat2 v.2.1.0 as aligner with default parameters.

A count table was produced using featureCounts v1.5.3 with default parameters.

To identify differentially expressed genes (DE genes), we used R (version 3.4.3) and the DESEq2 library (v. 1.18.1). Genes annotation were retrieved using the AnnotationDbi library (v. 1.40.0). Briefly, the count matrix produced by FeatureCounts was analysed by the DESegDataSetFromMatrix( ) function followed by the DEseq( ) function from the DESeq2 library. For each condition (i.e. comparison NTZ+CDAA/c vs CDAA/c), the fold change and the p-value were retrieved using the results( )function from DESeq2. The different tables were merged using the Ensembl ID as a key.

Histology

At sacrifice, liver samples were processed for histological analysis and examined as follows.

Tissue Embedding and Sectioning

The liver slices were first fixed for 40 hours in formalin 4% solution followed by several dehydration steps in ethanol (successive baths at 70, 80, 95 and 100% ethanol). The liver pieces were subsequently incubated in three xylene baths followed by two baths in liquid paraffin (58° C.). Liver pieces were then put into small racks that were gently filled with Histowax® to completely cover the tissue. Then, tissue samples were thicked in 3 μm sections. Sections were prepared for immunohistochemistry (IHC).

Immunohistochemistry Assay: CD3+

Immunohistochemistry assay was performed by using an immunoperoxidase protocol. Sections were dewaxed at 58° C. and in xylene baths (2×3 min). The specimens were hydrated ethanol (successive baths at 100%, 100%, 95% and 70%) (3 min each) and submerged in 1×PBS (2×5 min). Subsequently, endogenous peroxidase was blocked with H2O2 solution (0.3% H2O2 in distilled water) for 30 min, followed by three washes in 1×PBS for 5 min. Furthermore, heat mediated antigen retrieval was performed with citrate buffer at pH 6.0 for 40 min at 95° C. To block nonspecific binding, 1×PBS solution with 3% normal goat serum and 0.1% Triton was added for 60 min. Subsequently, the tissues were incubated with primary CD3 antibody overnight at 4° C. and rinsed with 1×PBS (3×5 min). The tissues were incubated with HRP secondary antibody (Novus Biological) for 1 h at room temperature and then rinsed with 1×PBS (3×5 min). Slides are then revelated with the peroxidase substrate 3,3'-diaminobenzidine ((DAB) for 20 min, and rinsed with tap water. Finally, the stains were counterstained with Mayer hematoxylin for 3 min and rinsed with tap water (2 min) and tissues were dehydrated in ethanol and xylene.

CD3+ IHC Analysis:

The histological examinations and scoring were performed blindly. Images were acquired using Pannoramic 250 Flash II digital slide scanner (3DHistech). Scoring: ten randomly selected fields from each section were examined and analyzed in QuPath software. The positive cells which were stained into brown were presented by the mean of positive cells/selected fields.

Results

Nitazoxanide, elafibranor or a combination of both drugs were evaluated in a fibrosing NASH model. Transcriptomics analyses of liver samples revealed that several markers associated with T cells infiltration and activation were significantly induced by the CDAA/c regimen in comparison with the CSAA control condition (CD3g, Clelc4e, IL12b). Unexpectedly, the ELA/NTZ combination reduces significantly the mRNA levels of these markers.

To confirm those data, immunohistochemistry analyses were performed. Accordingly, a significant increase of CD3 staining reflecting T cells number is observed comparing the CDAA/c group vs CSAA. As for the transcriptomics analyses, only the ELA/NTZ combination reduces significantly the amount of the CD3+ cells.

Altogether, those data illustrate the unexpected potency of the ELA/NTZ combination to prevent T Cells infiltration into the liver.

The invention claimed is:

1. A method for reducing or stopping immune cell infiltration into a tissue or organ in a subject, the method comprising administering to the subject a combination of:
(i) a compound of formula (I) or a pharmaceutically acceptable salt thereof:

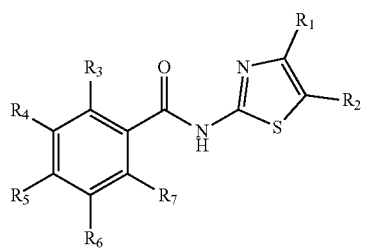

in which:
R1 represents a hydrogen atom, a deuterium atom, a halogen atom, a (C6-C14) aryl group, a heterocyclic group, a (C3-C14)cycloalkyl group, a (C1-C6)alkyl group, a sulfonyl group, a sulfoxyde group, a (C1-C6)alkylcarbonyl group, a (C1-C6)alkyloxy, a carboxylic group, a carboxylate group, a nitro group (NO2), an amino group (NH2), a (C1-C6)alkylamino group, an amido group, a (C1-C6)alkylamido group or a (C1-C6)dialkylamido group;

R2 represents a hydrogen atom, a deuterium atom, a NO2 group, a (C6-C14) aryl group, a heterocyclic group, a halogen atom, a (C1-C6)alkyl group, a (C3-C14)cycloalkyl group, a (C2-C6)alkynyl group, a (C1-C6)alkyloxy group, a (C1-C6)alkylthio group, a (C1-C6)alkylcarbonyl group, a (C1-C6)alkylcarbonylamino group, a (C6-C14) arylcarbonylamino group, a carboxylic or carboxylate group, an amido group, a (C1-C6)alkylamido group, a (C1-C6)dialkylamido group, a NH2 group or a (C1-C6)alkylamino group;

or R1 and R2, together with the carbon atoms to which they are attached, form a substituted or unsubstituted 5- to 8-membered cycloalkyl, heterocyclic or aryl group;

R3, R4, R5, R6, and R7, identical or different, represent a hydrogen atom, a deuterium atom, a halogen atom, a hydroxyl group, a (C1-C6)alkylcarbonyl group, an (C1-C6)alkyl group, an (C1-C6)alkyloxy group, an (C1-C6)alkylthio group, an (C1-C6)alkylcarbonyloxy group, an (C6-C14) aryloxy group, a (C6-C14) aryl group, a heterocyclic group, a (C3-C14)cycloalkyl group, a NO2 group, a sulfonylaminoalkyle group, an NH2 group, an amino (C1-C6)alkyl group, an (C1-C6)alkylcarbonylamino group, a carboxylic group, a carboxylate group, or a R9 group;

R9 represents a O-R8 group or an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or a moiety of formula (A):

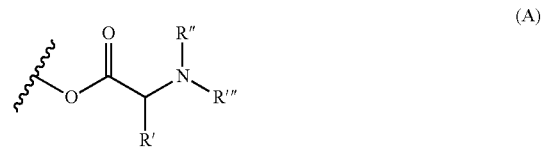

wherein R' represents an (C1-C6)alkyl group, an (C2-C6)alkenyl group, an (C2-C6)alkynyl group, a (C3-C14)cycloalkyl group, (C3-C14)cycloalkylalkyl group, a (C3-C14)cycloalkyl(C2-C6)alkenyl group, a (C3-C14)cycloalkenyl group, a (C3-C14)cycloalkenyl(C1-C6)alkyl group, a (C3-C14)cycloalkenyl(C2-C6)alkenyl group or a (C3-C14)cycloalkenyl(C2-C6)alkynyl group; wherein R" and R''', independently, represent a hydrogen atom, an (C1-C6)alkyl group, or a nitrogen protecting group; and R8 represents a hydrogen atom, a deuterium atom, a glucuronidyl group, or a

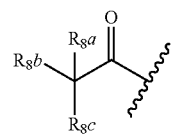

group wherein, R8a, R8b and R8c, identical or different, represent a hydrogen atom or a deuterium atom; and
(ii) a compound of formula (II) or a pharmaceutically acceptable salt thereof:

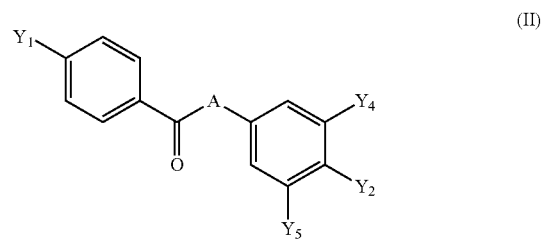

in which:
Y1 represents a halogen, a Ra, or Ga-Ra group;
A represents a CH=CH or a CH2-CH2 group;
Y2 represents a Gb-Rb group;
Ga and Gb, identical or different, represent an atom of oxygen or sulfur;
Ra represents a hydrogen atom, an unsubstituted (C1-C6)alkyl group, a (C6-C14) aryl group or a (C1-C6)alkyl group that is substituted by one or more halogen atoms, a (C1-C6)alkoxy or a (C1-C6)alkylthio group, (C3-C14)cycloalkyl groups, (C3-C14)cycloalkylthio groups or heterocyclic groups;
Rb represents a (C1-C6)alkyl group substituted by at least a -COORc group, wherein Rc represents a hydrogen atom, or a (C1-C6)alkyl group that is substituted or not by one or more halogen atoms, (C3-C14)cycloalkyl groups, or heterocyclic groups; and
Y4 and Y5, identical or different, representing a (C1-C6)alkyl group that is substituted or not by one or more halogen atoms, (C3-C14)cycloalkyl groups or heterocyclic groups.

2. The method according to claim 1, wherein the tissue or organ is the liver.

3. The method according to claim 1, for reducing or stopping NASH-associated immune cell infiltration into the liver, NAFLD-associated immune cell infiltration into the liver, ASH-associated immune cell infiltration into the liver, PBC-associated immune cell infiltration into the liver, or PSC-associated immune cell infiltration into the liver.

4. The method according to claim 1, for reducing or stopping T cell infiltration.

5. The method according to claim 1, for reducing or stopping T cell infiltration into the liver.

6. The method according to claim 1, for reducing or stopping NASH-associated T cell infiltration into the liver.

7. The method according to claim 1, wherein the compound of formula (I) is nitazoxanide or a pharmaceutically acceptable salt thereof.

8. The method according to claim 1, wherein the compound of formula (II) is elafibranor or a pharmaceutically acceptable salt thereof.

9. The method according to claim 1, wherein the combination is a pharmaceutical composition comprising the compound of formula (I), the compound of formula (II) and a pharmaceutically acceptable carrier.

10. The method according to claim 1, wherein the combination is a kit comprising the compound of formula (I) and the compound of formula (II), for sequential, separate or simultaneous use.

* * * * *